United States Patent [19]
Cummins et al.

[11] Patent Number: 5,874,213
[45] Date of Patent: Feb. 23, 1999

[54] CAPILLARY ELECTROPHORETIC DETECTION OF NUCLEIC ACIDS

[75] Inventors: Lendell L. Cummins; Susan M. Freier, both of San Diego; Richard Griffey, San Marcos; G. Susan Srivatsa, San Diego, all of Calif.

[73] Assignee: Isis Pharmacueticals, Inc., Carlsbad, Calif.

[21] Appl. No.: 469,852

[22] Filed: Jun. 6, 1995

Related U.S. Application Data

[62] Division of Ser. No. 295,509, Aug. 24, 1994.

[51] Int. Cl.$^6$ ..................................................... C12Q 1/68
[52] U.S. Cl. ................................. 435/6; 422/50; 422/62; 422/68.1; 422/69; 422/82.05; 435/286.1; 435/287.1; 435/287.2; 435/289.1; 436/501; 530/350; 536/25.3; 536/25.4; 935/77; 935/78; 935/88
[58] Field of Search ..................................... 435/5, 6, 290, 435/291, 810, 286.1, 287.1, 287.2, 289.1; 436/501; 536/22.1, 23.1, 24.1, 24.3–24.33, 25.3, 25.4; 530/350; 935/77, 78, 88; 422/50, 62, 68.1, 69, 82.05

[56] References Cited

FOREIGN PATENT DOCUMENTS

WO 86/05518  9/1986  WIPO .

OTHER PUBLICATIONS

Chen et al., "Identification on DNA Molecules by Pre-Column Hybridization Using Capillary Electrophoresis", J. of Chromatography 559: 295–305 (1991).

Goodchild, "Conjugates of Oligonucleotides and Modified Oligonucleotides: A Review of Their Synthesis and Properties", Bioconjuage Chemistry vol. 1: 165–187 (1990).

Huang et al., "Bias in Quantitative Capillary Zone Electrophoresis Caused by Electrokinetic Sample Injection", Anal. Chem. 60: 375–377 (1988).

Luckey et al., "High Speed DNA Sequencing By Capillary Electrophoresis", Nucleic Acids Research 18: 4417–4421 (1990).

McCord et al., "Capillary Electrophoresis of Polymerase Chain Reaction–Amplified DNA Using Fluorescence Detection with an Intercalating Dye", J. of Chromatography A 652: 75–82 (1993).

Rose, "Characterization of Antisense Binding Properties of Peptide Nucleic Acids by Capillary Gel Electrophoresis", Anal. Chem. 65: 3545–3549 (1993).

Janson & Ryden, Eds., *Protein Purification: Principles High Resolution Methods and Applications.*, Ch. 17 "Capillary Electrophoretic Separations" (Thormann and Firestone), VCH Publishers, New York, New York (1989).

Matthews et al. (1988) Analytical Biochemistry, vol. 169, pp. 1–25.

*Primary Examiner*—Ardin H. Marschel
*Attorney, Agent, or Firm*—Woodcock Washburn Kurtz Mackiewicz & Norris, LLP

[57] ABSTRACT

Methods are provided for detection and quantitation of mixtures containing target nucleobase sequences using capillary electrophoresis. Peptide nucleic acid oligomers, complementary to the target sequences and preferably having appended detectable labels, are hybridized to the targets. Capillary electrophoresis is then performed, and the detectable label is detected and quantitated.

35 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20 bases
        ( B ) TYPE: nucleic acid
        ( C ) STRANDEDNESS: single (D) TOPOLOGY: linear (xi) SEQUENCE DESCRIPTION: SEQ ID NO:1:

TCTGAGTAGC AGAGGAGCTC                                                                                           20

(2) INFORMATION FOR SEQ ID NO:2:

(i) SEQUENCE CHARACTERISTICS:
        (A) LENGTH: 19 bases
        (B) TYPE: nucleic acid
        (C) STRANDEDNESS: single
        (D) TOPOLOGY: linear (xi) SEQUENCE DESCRIPTION: SEQ ID NO:2:

TTTTTTTTT TTTTTTTT                                                                                              19

(2) INFORMATION FOR SEQ ID NO:3:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:3:

TGCATCCCCC AGGCCACCAT                                                                                           20

(2) INFORMATION FOR SEQ ID NO:4:

(i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO:4:

TTTTTTTTT TTTTTTT                                                                                               18

CAPILLARY ELECTROPHORETIC DETECTION OF NUCLEIC ACIDS

This is a division of application Ser. No. 08/295,509, filed Aug. 24, 1994.

FIELD OF THE INVENTION

The present invention relates to the field of diagnostic and analytic methods for detection and identification of nucleic acid species having specific nucleobase sequences, and to the use of capillary electrophoresis for such detection.

BACKGROUND OF THE INVENTION

Oligonucleotides of known sequence are utilized in a wide variety of chemical and biological applications, including PCR (polymerase chain reaction) and cloning, as well as in the diagnosis and treatment of diseases (see, for example, *Antisense Research and Applications*, Crooke and Lebleu, eds., CRC Press, Boca Raton, 1993). It is often desirable to detect or isolate a specific, desired oligonucleotide from complex mixtures which may include oligonucleotide species having nucleobase sequences closely related to those of the desired oligonucleotide. This is especially important in biological samples, where the presence or absence of specific known nucleotide sequences can be indicative of presence or absence of an added oligonucleotide agent or, alternatively, a disease state. It is also very important in the manufacture of oligonucleotides for characterization of the purity of the product.

However, samples of interest often do not contain sufficient concentrations of oligonucleotides to permit detection by techniques such as ultraviolet (UV) spectroscopy or they contain other absorbing species that prohibit detection of the species of interest. Other analytic techniques may lack specificity for a particular nucleic acid sequence, or require excessive sample preparation or analysis times. Thus, there exists a need for a method, which does not have the aforementioned limitations, of detecting and isolation of oligonucleotides containing specific, known nucleotide sequences.

The use of electrophoretic techniques to separate oligonucleotide species is documented in the literature. One such technique is capillary electrophoresis (CE), which employs relatively long and thin capillary columns for the separation. See generally, *Capillary Electrophoresis Theory and Practice*, P. Grossman and L. Colburn, eds. Academic Press, New York (1992). The CE technique affords several advantages over conventional electrophoretic techniques such as polyacrylamide gel electrophoresis (PAGE). As CE is performed in very small diameter tubing (typically 50–100 $\mu$m i.d.), electric fields 10 to 100 fold greater than those applicable in conventional electrophoretic systems can be applied because of reduced Joule heating. This affords very high speeds and superior resolution. Also, the CE technique lends itself to on-column detection by means such as ultraviolet spectroscopy, fluorescence spectroscopy, amperometric measurement, conductivity measurement or thermooptical detection. Additionally, CE can be performed with or without a gel medium in the capillary. When a gel medium such as polyacrylamide is employed, the technique is referred to a capillary gel electrophoresis (CGE).

There have been several reports of the use of CE in the detection of DNA species. For example, Luckey et al., *Nucleic Acids Research* 18 (15) 4417–4421 (1990) discloses a CE instrument developed for automated DNA sequencing in which products are detected via the fluorescence of an intercalating dye.

McCord et al., *J. Chromatography* 652 75–82 (1993) report the use of non-gel sieving buffers and fluorescent intercalating dyes in the CE analysis of PCR amplified DNA. Chen et al., *Journal of Chromatography*, 559, 295–305 (1991) describe the identification of DNA molecules by pre-column hybridization followed by capillary electrophoresis with on-line fluorescence detection.

Rose, *Anal. Biochem.* 65, 3545–3549 (1993) describes the use of CGE to separate peptide nucleic acid-oligonucleotide heteroduplexes from free single-strand oligonucleotide and single strand peptide nucleic acid (PNA). PNAs are capable of hybridization to complementary DNA or RNA sequences to form hybridized moieties which are more stable (i.e., which have higher binding affinities and higher melting temperatures) than corresponding "natural" duplexes. See *Antisense Research and Applications*, Crooke and Lebleu, eds., CRC Press, Boca Raton, 1993.

One disadvantage of the CE separation technique thus far has been the inherently irreproducible nature of the electrokinetic loading process. This results in the inability to quantitate the separated moieties. In the electrokinetic injection technique, the sample contents load onto the capillary both in response to the applied electric field, and by capillary action. Thus for most samples relatively small differences in the amounts of buffer salts present in the sample and an external standard can lead to dramatic differences in the amount of oligonucleotide loaded onto the column and the observed detector response. See Huang, X. et al., Anal. Chem. 60 375–377 (1988).

Thus, it would be of great advantage to have an analytical technique wherein the resolving power and superior resolution of CE could be applied in a quantitative fashion to the separation of oligonucleotide targets of similar length.

OBJECTS OF THE INVENTION

It is an object of the present invention to provide methods for the detection and identification of nucleic acid species having specific desired nucleobase sequences.

It is another object of the invention to provide capillary electrophoretic techniques to the isolation and separation of oligonucleotides containing specific desired nucleobase sequences.

It is another object of this invention to provide quantitative capillary electrophoretic techniques for such isolations.

BRIEF SUMMARY OF THE INVENTION

In accordance with these and other objects, the present invention provides methods for detecting oligonucleotides in quantitative fashion by capillary electrophoretic techniques. These oligonucleotides can be derived from either natural sources or synthetic sources. They include oligonucleotides that are cleavage products from larger nucleic acids including both DNA and RNA. Thus as used in this specification and its appended claims, such oligonucleotides, either natural or synthetic, can be collectively referenced as target oligonucleotides.

In one aspect of the invention methods are provided for detecting a target oligonucleotide, having a sequence of nucleosidic bases, in mixtures. The methods include the steps of selecting a first mixture suspected of containing the target oligonucleotide; forming a second mixture by contacting the first mixture with an oligomer having a sequence of nucleosidic bases that is complementary to at least a portion the sequence of nucleosidic bases of the target oligonucleotide; loading at least a portion of the second mixture onto a capillary electrophoresis column; and performing capillary electrophoresis on said column for a time and under conditions effective to separate hybridized moieties formed between the target oligonucleotide and the oligomer from unhybridized oligomer.

Preferred embodiments further comprise the step of detecting the separated hybridized moieties, preferably by ultraviolet spectroscopy, CE-mass spectroscopy, amperometric measurement, conductivity measurement, thermooptical detection or radioisotopic detection, with fluorescence detection being especially preferred.

In certain preferred embodiments the amount of hybridized moieties contained in the portion of the second mixture is quantitated, and in more preferred embodiments the amount of hybridized moieties is related to the amount of target oligonucleotide contained in the first mixture. In especially preferred embodiments the quantitating step is performed using an internal standard.

The detecting step preferably further includes contacting the hybridized moieties with an intercalating dye, preferably a fluorescent intercalating dye. Particularly preferred intercalating dyes include ethidium bromide, TOTO-1, YOYO-1 and thiazole orange.

In certain preferred embodiments the oligomer further includes a detectable label, preferably a fluorophore or an intercalating dye, more preferably fluorescein, dansyl, fluorescamine, OPA, NDA, ethidium bromide, acridine, JOE, FAM or rhodamine.

Some preferred embodiments further include the step of quantitating the amount of the fluorophore and relating the amount of the fluorophore to the amount of the target oligonucleotide present in the first mixture. In especially preferred embodiments at least one of the detecting step and the quantitating step is performed by using fluorescence measurement. The fluorescence measurement preferably is taken using on-column detection.

In some preferred embodiments the oligomer and the target oligonucleotide are of substantially the same length, and in other preferred embodiments the oligonucleotides in the first mixture are of substantially the same length.

In some preferred embodiments the oligomer has a length equivalent to the longest oligonucleotide in the first mixture and is complementary to the longest oligonucleotide, and in other preferred embodiments the nucelosidic base sequence of the target oligonucleotide is known.

In certain preferred embodiments the target oligonucleotide is part of the DNA or RNA nucleic acid of a pathogen, particularly an infective agent. Such infective agents include, as for example, bacterial, fungal, protozoa and viral agents. Included viral agents would include, among others, papillomavirus, herpes virus, cytomegalovirus, influenza virus hepatitis C virus, HIV virus or epstein barr virus.

In some preferred embodiments the electrophoresis is preformed by capillary gel electrophoresis wherein the capillary preferably containing polyacrylamide gel. In other preferred embodiments the electrophoresis is capillary zone electrophoresis.

In another aspect of the invention there are provided methods for detecting the presence of a target oligonucleotide having a sequence of nucleosidic bases which includes the steps of:

selecting a first mixture suspected of containing the target oligonucleotide; forming a second mixture by contacting the first mixture with a peptide nucleic acid of formula:

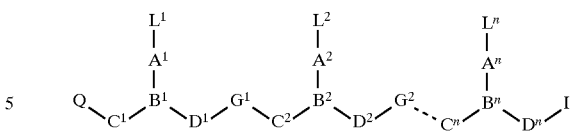

wherein:

n is at least 2, each of $L^1$-$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and detectable labels, at least one of $L^1$-$L^n$ being a naturally occurring nucleobase, a non-naturally occurring nucleobase, a DNA intercalator, or a nucleobase-binding group;

each of $C^1$-$C^n$ is $(CR^6R^7)_y$ where $R^6$ is hydrogen and $R^7$ is selected from the group consisting of detectable labels and the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, carboxy, ($C_1$–$C_2$) alkyl carboxy, ($C_1$–$C_6$) alkoxy, ($C_1$–$C_6$) alkylthio, $NR^3R^4$ and $SR^5$, where each $R^3$ and $R^4$ is independently selected from the group consisting of hydrogen, ($C_1$–$C_6$)alkyl, hydroxy- or alkoxy- or alkylthio-substituted ($C_1$–$C_4$)alkyl, hydroxy, alkoxy, alkylthio, detectable labels and amino, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is $(CR^6R^7)$ where $R^6$ and $R^7$ are as defined above;

each of y and z is zero or an integer from 1 to 10, the sum y+z being greater than 2 but not more than 10;

each of $G^1$-$G^{n-1}$ is —$NR^3CO$—, —$NR^3CS$—, —$NR^3SO$—, —$NR^3SO_2$—, in either orientation, where $R^3$ is as defined above;

each pair of $A^1$-$A^n$ and $B^1$-$B^n$ are selected such that:

(a) A is a group of formula (IIa), (IIb) or (IIc) and B is N or $R^3N^+$; or (b) A is a group of formula (IId) and B is CH;

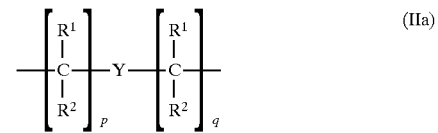

(IIa)

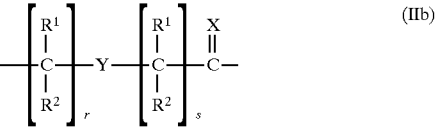

(IIb)

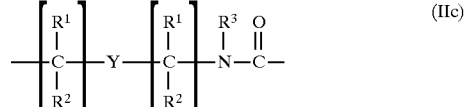

(IIc)

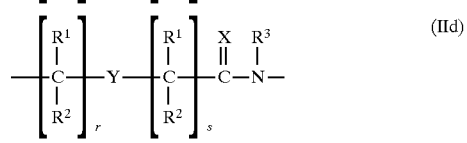

(IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino, detectable labels and halogen;

each of $G^1$-$G^{n-1}$ is —$NR^3CO$—, —$NR^3CS$—, —$NR^3SO$— or —$NR^3SO_2$—, in either orientation, where $R^3$ is as defined above;

Q is —$CO_2H$, —$CONR'R''$, —$SO_3H$ or —$SO_2NR'R''$ or an activated derivative of —$CO_2H$ or —$SO_3H$; and I is —$NHR'''R''''$ or —$NR'''C(O)R''''$, where R', R'', R''' and R'''' are independently selected from the group consisting of hydrogen, alkyl, amino protecting groups, detectable labels, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;

the peptide nucleic acid being complementary to at least a portion of the nucleosidic base sequence of the target oligonucleotide;

(b) loading at least a portion of the second mixture onto a capillary electrophoresis column; and (c) performing capillary electrophoresis on the column for a time and under conditions effective to separate hybriized moieties formed betwen the target oligonucleotide and the oligomer from unhybridized oligomer.

In preferred embodiments of the methods of the invention the peptide nucleic acid has the formula:

wherein:

each L is independently selected from the group consisting of hydrogen, phenyl, heterocyclic moieties, naturally occurring nucleobases, non-naturally occurring nucleobases and detectable labels;

each $R^{7'}$ is, independently, hydrogen, a side chain of a naturally occurring alpha amino acid, or Z, wherein Z is a detectable label;

n is an integer from 1 to 50;

each of k, l, and m is independently zero or an integer from 1 to 5;

p is zero, 1, or 2;

$R^h$ is OH, $NH_2$, OZ or -NHZ; and $R^i$ is H or Z; and $R_N$ is H or Z.

In certain preferred embodiments each L is independently selected from the group consisting of the nucleobases thymine (T), adenine (A), cytosine (C), guanine (G) and uracil (U); k and m are zero or 1; and n is an integer from 1 to 30. In other preferred embodiments said C, B, D and G groups together are 2-aminoethylglycine.

Some preferred embodiments further include the isolation and recovery of the hybridized moieties. Other preferred embodiments further include the isolation and recovery of the target oligonucleotide in substantially pure form.

Also provided in accordance with the invention are methods for detecting a target oligonucleotide having a sequence of nucleosidic bases, comprising the steps of selecting a mixture suspected of containing said target oligonucleotide; loading said mixture onto a capillary electrophoresis column

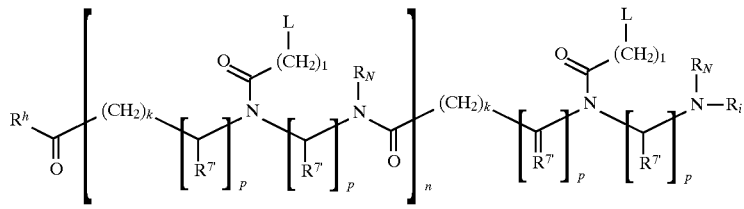

or formula:

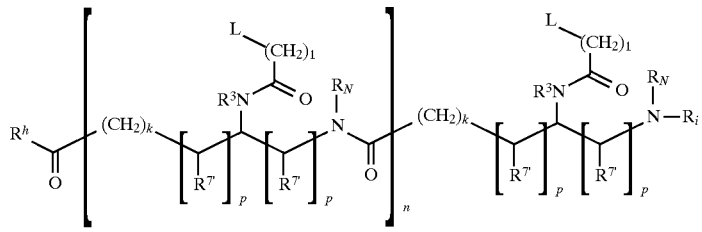

or formula

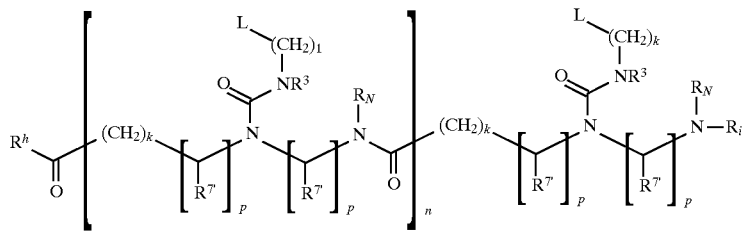

comprising an oligomer having a sequence of nucleosidic bases that is complementary to at least a portion said sequence of nucleosidic bases of said target oligonucleotide; and performing capillary electrophoresis on said column for a time and under conditions effective to separate hybridized moieties formed between said target oligonucleotide and said oligomer from unhybridized oligomer. In preferred embodiments the oligomer is a peptide nucleic acid.

In preferred embodiments methods are provided for diagnosing a biological sample comprising detecting a target oligonucleotide according to the methods of the invention. In other preferred embodiments methods are provided for analyzing a synthetic oligonucleotide sample comprising detecting a target oligonucleotide according to the methods of the invention.

In further preferred embodiments methods are provided for diagnosing a disease state comprising selecting a target oligonucleotide indicative of the disease state; and detecting said target oligonucleotide according to the methods of the invention. Preferably said target oligonucleotide forms a part of the nucleic acid of an organism implicated to cause said disease state.

DETAILED DESCRIPTION OF THE PREFERRED EMBODIMENTS

This invention provides novel methods for the detection and isolation of nucleic acids, nucleic acid fragments or other nucleic acid like species that have specific nucleobase sequences—hereinafter referee to as "target oligonucleotides" or "targets". In particular, the invention provides methods for detecting a target oligonucleotide in a mixture containing a plurality of other oligonucleotides or other like species that are similar in length to the target oligonucleotide, as is often the case in biological and research samples.

In preferred embodiments of the invention a mixture of nucleic acids, nucleic acid fragments, natural oligonucleotides, synthetic oligonucleotides or synthetic oligonucleosides or mixtures of one or more of these molecular species containing a target oligonucleotide is first contacted with a oligomer having a nucleobase sequence that is complementary to that of the target, i.e. capable of hybridizing to the target, to form a hybridized moiety that contains the oligomer-target hybrids. At least a portion of the mixture is then loaded onto a capillary electrophoresis column and capillary electrophoresis is performed to separate the hybridized moieties from any remaining components in the mixture.

In one sense, as used herein, the term "target oligonucleotide" refers to an oligomer or polymer of either ribonucleic acid (RNA) or deoxyribonucleic acid (DNA). This term includes oligomers that contain the naturally occurring nucleic acid nucleobases adenine (A), guanine (G), thymine (T), cytosine (C) and uracil (U); that contain the naturally occurring sugars ribose and deoxyribose and that contain the naturally occurring intersugar (backbone) phosphodiester linkages. In certain preferred embodiments, target oligonucleotides of the invention are the abovementioned naturally occurring phosphodiester linked ribonucleotides or dexoyribonucleotides.

In a further sense the term "target oligonucleotide" may include non-naturally occurring oligonucleotides, synthetic oligonucleotides, and even synthetic oligonucleosides. As used herein, non-naturally occurring oligonucleotides are oligonucleotides which contain nucleobase sequences which do not occur in nature, or species which contain functional equivalents of naturally occurring nucleobases, sugars or inter-sugar linkages. Oligonucleosides embrace non-phosphate containing inter-sugar linkages.

Naturally occurring nucleobases are defined herein as those which occur naturally in living entities, including the nucleobases adenine (A), guanine (G), thymine (T), cytosine (C) and uracil (U). Other "minor" nucleobase are also known in the nucleic acid literature. Non-naturally occurring nucleobases are synthetic molecular moieties which mimic the biological or chemical function of naturally occurring nucleobases with respect to their base-recognition and binding properties.

In preferred embodiments the target oligonucleotides are of known nucleobase sequence. The target oligonucleotides may be comparable in length to other nucleotide species in the sample of interest, or may be of different length. In certain preferred embodiments of the invention the target oligonucleotide is substantially the same length as the other oligonucleotide species in the sample, while in certain other preferred embodiments the target oligonucleotide has substantially the same length as the longest nucleotide species expected to be present in a sample.

Target oligonucleotides can derive from a variety of sources such as viral, bacterial and eukaryotic DNAs and RNAs. In certain preferred embodiments, target oligonucleotides are those that indicate the presence of disease, or that code for a protein that indicates the presence of a disease. Other target sequence can be derived during the manufacture of oligonucleotides and oligonucleosides as, for instance, any of the multiple oligonucleotides that are being manufactured for use as research reagents (PCR primers and the like), diagnostic agents or one of the several oligonucleotides that are currently undergoing clinical trials as therapeutic agents. It is especially important in this last group of oligonucleotides to know the composition of the product including any "minor" species that may be present particularly so called "short mers," i.e. oligonucleotides less that full length.

"Oligomers" as used in the invention are non-naturally occurring oligomeric species which hybridize to target oligonucleotides. As used herein, hybridization is the sequence specific bonding of two species together based upon their sequences. Normally such bonding is via hydrogen bonding of the exo-cyclic functional groups and ring nitrogens of the heterocyclic nucleobases. Typical hydrogen bonding of nucleobases is via formation of Watson-Crick and/or Hoogsteen base pairs; however, other type of base pairs can also occur including G:A or G:T base pairing. In preferred embodiments, the hybridization of complementary oligomers to target oligonucleotides produces a hybridized moiety, which can be, for example, a RNA/oligomer duplex, or a DNA/oligomer triplex, or some other higher order structure such as a tetraplex. The hybridized moiety will have a different charge to mass ratio compared to the target oligonucleotide and thus have different electrophoretic characteristics than the target oligonucleotide. In addition thereto the preferred oligomers of the invention also have improved specificity and/or affinity as compared to an analogous complexes containing only naturally occurring complementary DNA or RNA oligomers. Such improved specificity and/or affinity is normally expressed as a higher melting temperature (Tm). Thus, preferred oligomers of the invention have greater binding specificity and/or binding affinity for targets than naturally occurring complementary oligonucleotides.

In certain preferred embodiments, the oligomers are substantially electrically neutral or positive species, i.e., species which do not contain multiple negative electronic charges such as those associated with the phosphodiester linkages found in DNA and RNA. Particularly preferred in this regard are peptide nucleic acids (PNAs) which contain a polyamide backbone in place of the sugar-phosphate backbone present in naturally occurring oligonucleotides. Representative PNA species are disclosed in U.S. application Ser. No. 08/054, 363, filed Apr. 26, 1993, and U.S. application Ser. No. 08/088,658, filed Jul. 2, 1993, as well as U.S. application Ser. No. 08/108,591, filed Jul. 27, 1993, the disclosures of which are hereby incorporated by reference, and corresponding PCT application EP/01219, filed May 22, 1992. Particularly preferred PNA species are those based on the aminoethylglycine backbone.

Oligomers according to the invention can include chemically bound labels to facilitate detection by a variety of well known techniques. The chosen technique will depend upon the properties of the detectable label. In preferred embodiments the labels are species which can be detected by fluorescence, ultraviolet or visible absorbance spectroscopy (UV/VIS), capillary electrophoresis-mass spectroscopy, amperometric detection, conductivity, circular dichroism or thermooptical detection. Other modes of detection which may be applicable to CE techniques are also contemplated to be within the invention.

Preferably, the detectable label is a fluorophore. A representative list of fluorophores includes fluorescein, dansyl, fluorescamine, OPA, NDA, ethidium bromide, acridine, JOE, FAM and rhodamine. Other fluorohores precursors are sold by Molecular Probes, Inc. Eugene, OR. A useful group of these are listed in PCT application WO 92/03464. Thus, as will be apparent to those of skill in the art, there exists a wide variety of commercially available fluorophores which are suitable for use in the present invention.

In other preferred embodiments of the invention the detectable label is an intercalating dye. Intercalators per se are known to those of skill in the art as planar molecules which interpose between base pairs in nucleic acids or similar structures. Preferably, the intercalating dye is a fluorophore, such as ethidium bromide, TOTO-1, YOYO-1 and thiazole orange. Other intercalators (as well as fluorohores) are discussed by Goodchild, J., *Bioconjugate Chemistry*, 1990, 1, 165. Other suitable intercalators also will be apparent to those skilled in the art.

Detectable labels according to the present invention also include molecular moieties that exhibit characteristic spectra which permit spectrophotometric detection or that produce a characteristic mass spectral fragment for detection in a mass spectrometer. Molecules that can be detected by conductivity, circular dichroism, thermooptical detection or amperometric detection also can be used as detectable labels. Sulfates, polylysines and polyglutamates are typical species useful for conductivity and amperometric detection. PEG groups (polyethylene glycols) are typical species useful for thermooptical detection while amino acids and other compounds carrying a chiral center are typical species useful for detection by circular dichroism. The detectable label is chemically bound to the complementary oligomer, usually via a covalent chemical bond. Aside from detectibilty, two requirements for a detectable label are: (1) it does not prohibit specific hybridization of the target oligonucleotide to a complementary oligomer, and (2) that it not impart to the resulting hybridized moiety undesired electrophoretic mobility characteristics, such as an excessive retention time. For some detectable labels, for example with intercalating dyes, the detectable label is expected to stabilize the hybridized moiety.

In preferred embodiments of the invention, separation of hybridized moieties from other components of a mixture or sample is achieved by capillary electrophoresis. As used herein, the term capillary electrophoresis is used in its normal sense and indicates electrophoretic separation performed in relatively low volume systems, such as narrow bore plastic tubes, glass capillaries, or thin fluid films between parallel plates. See generally Janson Ryden, *Protein Purification*, Ch. 17, VCH Publishers, New York, New York and *Capillary Electrophoresis Theory and Practice*, supra.

The methods of the invention can be practiced using commercially available electrophoretic apparatus, produced for example by LKB (Bromma, Sweden) and Beckman Instruments (Fullerton, Calif.). The methods of the invention also can be practiced using a wide variety of commercially available capillary electrophoresis columns.

Those in the art will appreciate that there are many capillary electrophoretic techniques that can be employed to detect and isolate hybridized moieties in accordance with the invention. These include but are not limited to capillary zone electrophoresis (CZE), discontinuous capillary zone electrophoresis (DCZE), capillary isotacophoresis (CITP), capillary isoelectric focusing (CIEF) and micellar electrokinetic capillary chromatography (MECC). See *Capillary Electrophoresis Theory and Practice*, supra.

Preferred embodiments of the invention employ capillary gel electrophoresis (CGE), wherein the electrophoresis capillary is filled with a gel. In preferred embodiments of CGE or QCGE the capillary is filled with polyacrylamide gel, that is a polymer of acrylamide including crosslinking agents routinely used in acrylamide polymerization. Other gel media known to those in the art as suitable for CGE are also expected to find use in the methods of the present invention.

Detection of separated hybridized moieties can be achieved by any of the many techniques known for use in capillary electrophoretic systems. In preferred embodiments detection of hybridized moieties is accomplished by on-column detection techniques. These include but are not limited to fluorescence, ultraviolet or visible absorbance spectroscopy (UV/VIS), capillary electrophoresis-mass spectroscopy, amperometric detection, conductivity, circular dichroism and thermooptical detection. In preferred embodiments detection is by fluorescence.

Quantitation of the detected hybridized moieties can be achieved by novel methods of the invention wherein both external and internal standards are used to correct for error introduced by column loading. These methods are hereinafter referred to as quantitative capillary electrophoresis (QCE) or, where the capillary contains a gel such as polyacrylamide, quantitative capillary gel electrophoresis (QCGE). As used hereinafter, the term QCE shall include both gel-containing and non-gel containing capillary electrophoretic systems.

In QCE, the external reference standard consists of the species to be detected (for example hybridized moieties) in a sample matrix. The sample matrix is preferably a solution identical to that of the sample, to overcome the inherent injection-to-injection irreproducibility of the loading technique. The internal sample, which is introduced into the sample itself, corrects for the inherent irreproducibility of migration times and peak areas.

Suitable internal standards for the practice of the invention preferably have solvent extraction properties similar to those of the target oligonucleotide and different migration times than the hybridized moieties. For ease of detection, normally, a internal standard having a faster migration time is selected. One such standard is a phosphorothioate $T_{18}$ oligomer having a 5'-fluoroscein moiety.

The QCE technique may be applied to any system wherein it is desired to quantitate products of capillary electrophoretic separations. For example, QCGE has been validated as an acceptable technique for the routine analysis of phosphorothioate drug formulations. See Srivatsa, S. G., Batt, M., Schuette, J., Carlson, R. Fitchett, J. Lee, C., and Cole, D. L., *J. of Chromagraphy*, in press.

As used herein, the term "detecting" means the identification of hybridized moieties by any of the physical or chemical means described herein, including ultraviolet spectroscopy, fluorescence spectroscopy, amperometric measurement, conductivity measurement, thermooptical detection and radioisotopic detection. See: *Capillary Electrophoresis Theory and Practice*, supra. The term CE-mass spectroscopy is meant to describe the process of performing routine mass spectral analysis on a product of CE separation. Mass spectroscopic detection of dimeric hybrids was recently presented in a poster by Gregg, M. et al., at the American Society for Mass Spectroscopy, Mass Spectroscopy and Allied Topics, Chicago, Ill., May, 1994.

In preferred embodiments of QCE the amount of hybridized moiety is related to the amount of target oligonucleotide. Such relating is preferably accomplished via procedures in which standard curves are employed to compensate for irreproducibilities inherent in the CE technique. For example, because the mobility of a given analyte depends upon its mass-to-charge ratio, migration velocities of the analytes will differ, resulting in differences in the residence time at the detector, and hence differences in peak areas. This is corrected for by dividing the observed peak area by the corresponding migration time to obtain a "corrected peak area."

There is also inherent irreproducibility in the loading of analytes by electrokinetic injection. This is caused by the preferential loading of small charged molecules such as buffer ions. To compensate for differences in sample loading between injections, the corrected peak area is further normalized to the detector response of an internal standard, such normalization being termed the "normalized peak area." The "normalized migration time" is then calculated by dividing the migration time of the analyte by that of the internal standard.

In preferred methods of the invention the complementary oligomer and the target oligonucleotide are of substantially the same length. As used herein, "substantially the same length" means having substantially the same number of nucleosidic bases. As for example, as is illustrated in the examples below, full length oligonucleotides were successfully separated from N-1 and N-3 short mers even at very low concentration in the nanomolar range. Of course, as the short mers become increasing shorter they become increasingly different from the parent full length target oligonucleotide. Thus for the purposes of this specification, substantially the same length shall mean at least N-3, N-2 and N-1 short mers as compared to full length oligonucleotide.

In a still further aspect of the invention, target oligonucleotides in a sample are detected using CGE and a column that has been pre-loaded with the oligomer. In practicing this embodiment, one or more oligomers having specific sequences are incorporate within the gel matrix of the capillary gel electrophoresis column. The oligomer, preferably one or more PNAs that includes one or more lysines or other species that can carry a net positive charge as well as a detection label, e.g. fluorescein, can be pre-loaded on the column either by direct incorporation in the gel matrix material or it can be loaded via an injection technique such as electrokinetic injection. After pre-loading the oligomer onto the column, the sample suspected of harboring the target oligonucleotide or oligonucleotides is loaded on the column and CGE is effected. If lysine-PNA is used as the oligomer, during CGE, since the lysine-PNA carries a net positive charge, it will move through the column opposite of that of the oligonucleotide species. The oligonucleotide species will encounter the PNA and if they are capable of duplexing, a duplex will be form and be carried toward the detector. Capillary gel electrophoresis is preformed on the sample and the column is monitored for one or more duplex species corresponding to duplexes between the target oligonucleotides and the oligomers incorporated in the column. In using a column that is loaded with the PNA incorporated directly in the gel, since the PNA will move in a direction opposite that of a negative charged oligonucleotide or duplex of an oligonucleotide and a PNA, prior to injection of the sample carrying or suspected to carry the target oligonucleotide, the column can be run in the forward direction (the same polarity that will be used to move the target through the column) until such time as all the PNA (carrying a detection label thereon) has cleared the detection zone in the column. Further electrophoretic movement of non duplex PNA will then be away from the detection zone area while movement of duplexed PNA will be towards the detector zone area. By using this technique, the duplexed species can be detected without undue background from un-duplexed PNA. In using a column wherein the PNA is loaded into the column by electrophoretic movement, the column is preferably loaded under conditions wherein the PNA will not located within the detection zone area. One method by which this can be accomplished is by pre-loading the PNA for a time sufficient to just load the PNA in the leading portion of the column between the end of the column wherein sample is loaded and the detector zone area.

Oligomers according to the invention preferably have from 5 to 50 nucleobases, with 10 to 30 nucleobases being preferred and 15 to 20 nucleobases being especially preferred.

Oigomers according to the invention can include one or more molecular species which facilitate the quality of separation or detection afforded by the methods of the invention. These species may be, for example, aromatic moieties, heterocyclic moieties, reporter ligands, alkyl groups, aralkyl groups or chelators.

Aromatic moieties, as used herein are molecular species having from three to ten carbons and which include an aromatic ring, such as a phenyl ring. Heterocyclic moieties are molecular species having from three to ten carbons and containing a ring which includes at least one non-carbon atom therein. Reporter ligands are molecular moieties which are capable of being detected by physical or chemical means, such as those means by which the detectable labels of the invention are detected.

As used herein, the term alkyl is meant to include straight-chain, branched and cyclic hydrocarbons such as ethyl, isopropyl and cyclopropyl groups, which may be substituted at one or more hydrogens by halide atoms or hydroxyl groups. Preferred alkyl groups include $C_1$ to $C_{20}$ alkyl with a more preferred group being $C_1$ to $C_6$ alkyl.

The term aralkyl means alkyl groups having appended thereto an aryl group. As used herein heteroaryl means an aromatic ring compound wherein at least one atom in the ring is a non-carbon atom. An alicyclic system as used herein is an aliphatic (i.e. saturated, hydrogen and carbon containing) ring such as cyclopropyl or cyclopentyl.

The amino groups of PNA oligomers may have protecting groups bound thereto. Protecting groups are known per se as chemical functional groups that can be selectively appended to and removed from chemical functionalities. These groups are present in a chemical compound to render such functionality inert to chemical reaction conditions to which the compound is exposed. Representative suitable amino protecting groups may be found in Greene, T. W. and Wuts, P. G. M., *"Protective Groups in Organic Synthesis"* 2d. Ed., Wiley & Sons, 1991.

As used herein chelators have their usual meaning as known in the art as compounds which coordinate strongly to metals. Representative chelators include EDTA, DTPA, and o-phenanthroline.

In preferred embodiments hybridized moieties and target oligonucleotides are isolated and recovered. Isolation is the physical separation of a hybridized moiety or target oligonucleotide from the other components of the sample such that it is detectable without the other components, for example as on the CE column by the techniques mentioned above. Recovery is the further physical separation such that the recovered hybridized moiety or target oligonucleotide exists substantially by itself in a sample.

In preferred embodiments the techniques of the invention are practiced such that the CGE is preformed at a temperature that is below the melting temperature of the PNA oligomer and its target oligonucleotide but above a temperature wherein the same target oligonucleotide might bind to complementary DNA or RNA. Since PNAs when hybridized to DNA or RNA strands typically have melting temperature that are at least 10° C. or more higher than those of the corresponding DNA:DNA, DNA:RNA or RNA:RNA hybrids, this insures that DNA:DNA, DNA:RNA or RNA:RNA species do not interfere with the formation of duplex (or other higher homolog) species between the PNA and its target oligonucleotide.

In preferred embodiments of the invention the techniques may be applied to analyze the purity of an oilgonucleotide during its manufacture. The techniques of the invention are particularly suited for the identification of short mers and the like which may exist as contaminating species in an manufactured sample.

In other preferred embodiments the techniques of the invention may be applied to genomic testing, as for example in the detection of a point modification. Such a modification can be detected by the methods of the invention and differentiated from a "wild type" normal gene. Examples of such point modifications are those which occur in RAS and other similar genes that induce undesirable effects when expressed in a host. Other such genomic testing for which the methods of the invention are useful include detecting of abnormal sequences indicative of abnormalities such as sickle cell anemia and other like diseases.

In preferred embodiments the techniques of the invention may be applied to the diagnosis of a disease state. In this context, the disease would be capable of diagnosis by the presence or absence of a particular known nucleotide sequence in the genome of the organism. Such diagnosis would normally include digestion or other like technique known in the art to cleave the genomic or message nucleic acid into fragments that include oligonucleotides of the lengths contemplated by this invention. Such cleavage could be specific to a particular sequence by using appropriate restriction enzymes known in the art for producing such a sequence. For speed of separation, normally, the cleavage product of interest would be in a size range of from 5 to about 200 nucleotide units in length. For further ease of separation a more preferred range would be from about 5 to about 50 nucleotides in length.

EXAMPLE 1

Column Preparation and Separation of Standard DNA Sequences By CGE

75 μM I.D., 360 μM O.D. capillary columns of fused silica of a total length of 40 cm and a 23 cm effective separation length (from injection end to detector window) were filled with polyacrylamide gel (via a syringe). Initial column were 8% polyacrylamide (0% crosslinking) in 7M urea and 100 mM Tris-Borate (designated as a 8% T, 0% C column). Running buffer was 7M urea and 100 mM Tris-Borate. Initial column testing was effected utilizing a standard composed of 1) a set of homothymidine oligonucleotides containing oligomer of approximately 10–25 mer size length and 2) a set of mixtures of a 21 mer mixed sequence phosphorothioate oligonucleotide containing one of various N-1 mer failure sequences in each member of the set. Injections were made at −5 kV for 2 seconds. Separations were made at 60° C. at −30 kV. These conditions resulted in a current of 7 to 8 μA. Peaks were detected by UV. Migration times of the separated oligomers of the sets were measured. Initial oligomer concentration were analyzed as 0.2 OD's/ml solutions. The various length oligomers in the homothymidine oligonucleotide test sequences were effectively separated in times varying from 4.4 mins to 6.2 mins. In each instance, the mixed sequence oligonucleotide was separated from its short mers. The parent peak was observed to elute around 6 min, with the migration time varying from about 5.8 to about 6.4 mins depending on the contaminating short mer sequence.

EXAMPLE 2

Separation of Standard PNA Sequences By CGE

Separations were effected on lysine derivatized PNA's as per the procedures of Example 1 except a low pH gel system was used to insure the lysine conjugate carried a charge (and also at least the C, G and A base were also protonated) giving a lower mass to charge ratio. The gel was a 10% T, 0% C, 5% acetic acid, 7M urea and 0.3% TRITON X-100 (t-octylphenoxypolyethoxyethanol) with 5% acetic acid as the running buffer. Injection was via electrokinetic injection. A 75 μM I.D. column having a 43 cm total length and a 23 effective length was used. Voltage was 20 kV at 18 μA start. Detection as effected at 260 nm, 0.05 RT, 0.005 AUFS at 45° C. A first mixed sequence purified PNA at a concentration of 500 μM was injected over 5 seconds. Run time was 7.185 minutes. A small impurity was detected at 18 minutes. A second mixed sequence PNA at a concentration of 0.5 OD/ml was injected over 20 seconds and showed a major peak at 20.006 minutes with minor peaks both before and after the major peak. The peaks of both samples compared to those observed in reverse phase HPLC with respect to both number and relative abundance.

EXAMPLE 3

Separation of PNA:DNA Duplex by CGE

A DNA of a specific sequence was analyzed by forming a heteroduplex with a fluoresceinated PNA. The duplex was formed by mixing the oligomers in $H_2O$ followed by analysis via CGE using laser induced fluorescence (LIF) detection. The PNA (of the sequence TCT GAG TAG CAG AGG AGC TC (SEQ. ID. NO: 1)) complementary to the target DNA sequence was synthesized as per published procedures having a lysine residue on its carboxyl terminus and a glycine on its amino terminus. Two hexanoic amine acids linkers were attached in series to the glycine residue with the fluorescein labeled attached to the amino terminus of the hexanoic amino acid linker. Analysis conditions used were as per Example 1 except the gel was 10% T, 0% C, separations were at 20° C., and column length was 27 cm total/20 cm effective length. Since detection was via LIF, only that DNA complexed with fluoresceinated PNA was detected. In a first electropherogram only PNA was injected. Under the test conditions no oligomer-related fluoresceinated material was detected, however, minor peaks were observed that are believed to represent a small contamination of free fluoresceinated impurities. DNA concentration was between approximately 1 μM and 200 nM, while PNA was maintained in slight stoichiometric excess. When complementary 20-mer DNA was added to the fluoresceinated PNA, a peak was observed. When mixtures of 18-, 19- and 20-mer DNA were added to the corresponding complementary 20 mer PNA, multiple peaks were observed in the resulting electropherograms representing the PNA:DNA duplexes formed with full-length, n-1 and n-2 DNA.

EXAMPLE 4

Specificity of PNA:DNA Duplex by CGE

The specificity of the PNA of Example 3 was determined against both a 19-mer homothymidine phosphorothioate oligonucleotide and a 15-mer mixed sequence phosphorothioate oligonucleotide that was not complementary to the PNA sequence. In both instances, the additions of these oligonucleotides did not form detectable duplexes with the PNA.

EXAMPLE 5

Resolution of PNA:DNA Duplex by CGE

The resolution of the PNA:DNA duplex of Example 3 was examined with freshly prepared 4% T, 0% C and 6% T, 0% C gels. The buffer was modified to Tris-Borate pH 7.5 (which was approximately 1 pH unit lower that the Tris-Borate of Example 3). Column length remained the same at 27 cm total/20 cm effective length. The resolution obtained was slightly improved over that of Example 3 for the 4% T column.

The effect of column temperature was examined using the 4% T column. At 30° C., the resolution was measured at 0.65. Increasing the temperature to 40° C. improved the resolution to 0.85 and increasing the temperature to 50° C. improved resolution to 0.91.

EXAMPLE 6

Resolution by CGE of Full Length, N-1 and N-3 DNA via PNA Duplexing

PNA duplexing was used to resolve a mixture of a full length 20-mer DNA from its N-1 and N-3 short mers. Conditions used were as described in Example 3 except a Beckman 100 μM eCAP 40 cm column was used. The CGE analysis was run at 14 kV and 30° C. PNA alone, DNA alone and a $T_{9-25}$ homothymidine oligonucleotide mixture served as controls. The PNA:N-1 and N-3 DNA short mers were fully resolved from each other as well as from the PNA:fully length DNA.

EXAMPLE 7

Quantitation of DNA Extracted from plasma using PNA:DNA Duplex Analysis by CGE Quantitation of DNA samples extracted from plasma and the resolution of full length verses N-1 short mers of this DNA duplexed with PNA was examined using the general protocols of Example 3. The column had a 20 cm effective length and a 100 μM ID; the gel was 10% T, 0% C, 100 mM Tris Borate, pH 8.5; and detection was by LIF (laser induced fluorescence). The CGE separations were carried out at −15 kV at 30° C. PNA used was of the sequence TGC ATC CCC CAG GCC ACC AT (SEQ. ID. NO: 2) and was fluoresceinated at its amino terminus as described in Example 3. The carboxyl terminus of the PNA included a lysine derivatized to a carboxamide. An 18-mer homothymidine oligonucleotide fluoresceinated at its 5' terminus ($T_{18}$-FITC) was used as a standard.

Samples of fully length DNA and N-1 DNA complementary to PNA of the sequence were prepared in plasma at concentrations of 1 μM, 500 nM, 250 nM, 100 nM, 50 nM, 5 nM and 500 pM with 100 nM $T_{18}$-FITC standard. The samples were extracted from the plasma by SAX chromatography and were desalted by reverse phase chromatography prior to vacuum evaporation to dryness. The samples were rehydrated to 40 μl in $H_2O$. Samples were then hybridized with approximately 10 fold excess PNA complement and analyzed by CGE. The electropherograms suggested that both fully length and N-1 species were bound by the PNA. Resolution was successful down to at least the 50 nM level. The unduplexed DNA was not detectable even at the 1 μM level.

EXAMPLE 8

Identification of Specific DNA Using CGE Column Incorporating PNA

A. Pre-Load PNA via incorporation of PNA in Gel

PNA as described in Example 3 in a concentration of 1 μM is added to polyacrylamide gel (10% T, 0% C) and 7M urea and is loaded in 100 μM I.D. column having a 23 cm effective length. Electrophoresis is effected until the laser-induced fluorescence falls to a constant baseline level, indicating that the labeled PNA species is no longer present within the detection zone area. CGE separation of the samples of Example 7 are carried out as per the protocol of Example 7.

B. Pre-Load PNA via Electrokinetic Injection

A 1 μM solution of PNA as described in Example 3 is continuously introduced into a 10% T, 0% C gel on a CGE column in the manner of Example 3 by reversing the voltage to load the PNA on to the column. PNA is loaded for a time sufficient to load the first third of the effective length of the column with PNA. Voltage polarity is then reversed and the DNA samples is loaded as per Example 3.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

---

What is claimed is:

1. A method for detecting a target oligonucleotide having a sequence of nucleosidic bases, comprising the steps of:
selecting a first mixture suspected of containing said target oligonucleotide;
forming a second mixture by contacting said first mixture with a peptide nucleic acid oligomer having a sequence of nucleosidic bases that is complementary to at least a portion said sequence of nucleosidic bases of said target oligonucleotide;
loading at least a portion of said second mixture onto a capillary electrophoresis column;
performing capillary electrophoresis on said column for a time and under conditions effective to separate hybridized moieties formed between said target oligonucleotide and said peptide nucleic acid oligomer from unhybridized oligomer; and
detecting said hybridized moieties, thereby detecting said target oligonucleotide.

2. A method for detecting a target oligonucleotide having a sequence of nucleosidic bases, comprising the steps of:
selecting a mixture suspected of containing said target oligonucleotide;
loading said mixture onto a capillary electrophoresis column wherein at least a portion of said column comprises a peptide nucleic acid oligomer having a sequence of nucleosidic bases that is complementary to at least a portion said sequence of nucleosidic bases of said target oligonucleotide; and
performing capillary electrophoresis on said column for a time and under conditions effective to separate hybridized moieties formed between said target oligonucleotide and said peptide nucleic acid oligomer from unhybridized oligomer; and
detecting said hybridized moieties, thereby detecting said target oligonucleotide.

3. The method of claim 1 further comprising the step of quantitating the amount of hybrizided moieties contained in said portion of said second mixture.

4. The method of claim 2 wherein said intercalating dye is a fluorophore.

5. The method of claim 3 wherein said fluorophore is ethidium bromide, TOTO-1, YOYO-1, or thiazole orange.

6. The method of claim 1 wherein said oligomer includes a detectable label.

7. The method of claim 5 wherein said detectable label is a fluorophore or an intercalating dye.

8. The method of claim 6 wherein said fluorophore is fluorescein, dansyl, fluorescamine, OPA (ortho-phthaldialdehyde), NDA (naphthalene-2',3'-dicarboxaldehyde), ethidium bromide, acridine, JOE (6-carboxy-4',5'-dichloro-2',7'-dimethoxyfluoroscein), FAM (5'-carboxyfluoroscein), or rhodamine.

9. The method of claim 1 wherein said electrophoresis is capillary zone electrophoresis.

10. The method of claim 1 wherein said detecting step is performed using ultraviolet spectroscopy, CE-mass spectroscopy, amperometric measurement, conductivity measurement, thermooptical detection or radioisotopic detection.

11. The method of claim 3 further comprising relating said amount of hybridized moieties to the amount of said target oligonucleotide contained in said first mixture.

12. The method of claim 3 wherein said quantitating step is performed using an internal standard.

13. The method of claim 1 wherein said detecting step further comprises contacting said hybridized moieties with an intercalating dye.

14. The method of claim 7 further comprising the step of quantitating the amount of said fluorophore and relating said amount of said fluorophore to the amount of said target oligonucleotide present in said first mixture.

15. The method of claim 14 wherein at least one of said detecting step and said quantitating step comprises a fluorescence measurement.

16. The method of claim 15 wherein said fluorescence measurement is taken using on-column detection.

17. The method of claim 1 wherein said oligomer and said target oligonucleotide are of substantially the same length.

18. The method of claim 1 wherein said mixture contains a plurality of oligonucleotides that are of substantially the same length.

19. The method of claim 1 wherein said mixture contains a plurality of oligonucleotides.

20. The method of claim 19 wherein said oligomer has a length equivalent to the longest oligonucleotide in said mixture and is complementary to said longest oligonucleotide.

21. The method of claim 1 wherein said nucleosidic base sequence of said target oligonucleotide is known.

22. The method of claim 1 wherein said target oligonucleotide has a nucleosidic base sequence that is contained within the nucleic acid of a pathogen.

23. The method of claim 22 wherein said pathogen is papilloma virus, herpes virus, cytomegalovirus, influenza virus hepatitis C virus, HIV virus or epstein barr virus.

24. The method of claim 1 wherein said electrophoresis is capillary gel electrophoresis.

25. The method of claim 9 wherein said capillary contains polyacrylamide gel.

26. The method of claim 1 wherein said peptide nucleic acid has formula:

$$Q\diagdown_{C^1}\diagup^{B^1}\diagdown_{D^1}\diagup^{G^1}\diagdown_{C^2}\diagup^{B^2}\diagdown_{D^2}\diagup^{G^2}\cdots_{C^n}\diagup^{B^n}\diagdown_{D^n}\diagup^{I}$$

with $L^1/A^1$ on $C^1$, $L^2/A^2$ on $C^2$, $L^n/A^n$ on $C^n$ wherein:

n is at least 2, each of $L^1$-$L^n$ is independently selected from the group consisting of hydrogen, hydroxy, $(C_1$-$C_4)$alkanoyl, naturally occurring nucleobases, non-naturally occurring nucleobases, aromatic moieties, DNA intercalators, nucleobase-binding groups, heterocyclic moieties, and detectable labels, at least one of $L^1$-$L^n$ being a naturally occurring nucleobase, a non-naturally occurring nucleobase, a DNA intercalator, or a nucleobase-binding group;

each of $C^1$-$C^n$ is $(CR^6R^7)_y$ where $R^6$ is hydrogen and $R^7$ is selected from the group consisting of detectable labels and the side chains of naturally occurring alpha amino acids, or $R^6$ and $R^7$ are independently selected from the group consisting of hydrogen, $(C_2$-$C_6)$alkyl, aryl, aralkyl, heteroaryl, hydroxy, carboxy, $(C_1$-$C_2)$ alkyl carboxy, $(C_1$-$C_6)$alkoxy, $(C_1$-$C_6)$alkylthio, $NR^3R^4$ and $SR^5$, where each $R^3$ and $R^4$ is independently selected from the group consisting of hydrogen, $(C_1$-$C_6)$alkyl, hydroxy- or alkoxy- or alkylthio-substituted $(C_1$-$C_4)$alkyl, hydroxy, alkoxy, alkylthio, detectable labels and amino, and $R^5$ is hydrogen, $(C_1$-$C_6)$alkyl, hydroxy-, alkoxy-, or alkylthio-substituted $(C_1$-$C_6)$alkyl, or $R^6$ and $R^7$ taken together complete an alicyclic or heterocyclic system;

each of $D^1$-$D^n$ is $(CR^6R^7)_z$ where $R^6$ and $R^7$ are as defined above;

each of y and z is zero or an integer from 1 to 10, the sum y+z being greater than 2 but not more than 10;

each of $G^1$-$G^{n-1}$ is —$NR^3CO$—, —$NR^3CS$—, —$NR^3SO$—, —$NR^3SO_2$—, in either orientation, where $R^3$ is as defined above;

each pair of $A^1$-$A^n$ and $B^1$-$B^n$ are selected such that:

(a) A is a group of formula (IIa), (IIb) or (IIc) and B is N or $R^3N^+$; or (b) A is a group of formula (IId) and B is CH;

$$\left[\begin{array}{c}R^1\\|\\-C-\\|\\R^2\end{array}\right]_p -Y- \left[\begin{array}{c}R^1\\|\\-C-\\|\\R^2\end{array}\right]_q \quad \text{(IIa)}$$

$$\left[\begin{array}{c}R^1\\|\\-C-\\|\\R^2\end{array}\right]_r -Y- \left[\begin{array}{c}R^1\\|\\-C-\\|\\R^2\end{array}\right]_s \begin{array}{c}X\\||\\-C-\end{array} \quad \text{(IIb)}$$

$$\left[\begin{array}{c}R^1\\|\\-C-\\|\\R^2\end{array}\right]_r -Y- \left[\begin{array}{c}R^1\\|\\-C-\\|\\R^2\end{array}\right]_s \begin{array}{c}R^3\;O\\|\;\;||\\-N-C-\end{array} \quad \text{(IIc)}$$

$$\left[\begin{array}{c}R^1\\|\\-C-\\|\\R^2\end{array}\right]_r -Y- \left[\begin{array}{c}R^1\\|\\-C-\\|\\R^2\end{array}\right]_s \begin{array}{c}X\;\;R^3\\||\;\;|\\-C-N-\end{array} \quad \text{(IId)}$$

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1$-$C_4)$alkyl which may be hydroxy- or alkoxy- or alkylthio-substituted, hydroxy, alkoxy, alkylthio, amino, detectable labels and halogen;

each of $G^1$-$G^{n-1}$ is —$NR^3CO$—, —$NR^3CS$—, —$NR^3SO$— or —$NR^3SO_2$—, in either orientation, where $R^3$ is as defined above;

Q is —$CO_2H$, —$CONR'R''$, —$SO_3H$ or —$SO_2NR'R''$ or an activated derivative of —$CO_2H$ or —$SO_3H$; and I is —$NHR'''R''''$ or —$NR'''C(O)R''''$, where R', R'', R''' and R'''' are independently selected from the group consisting of hydrogen, alkyl, amino protecting groups, detectable labels, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

27. The method of claim 26 wherein said peptide nucleic acid has the formula:

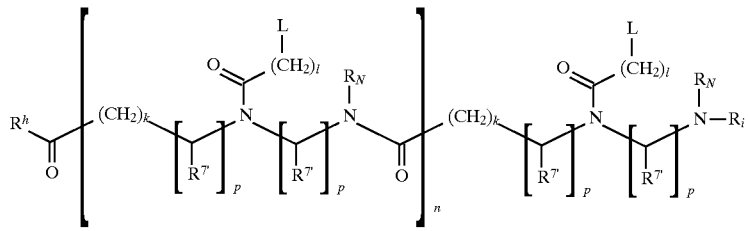

or formula

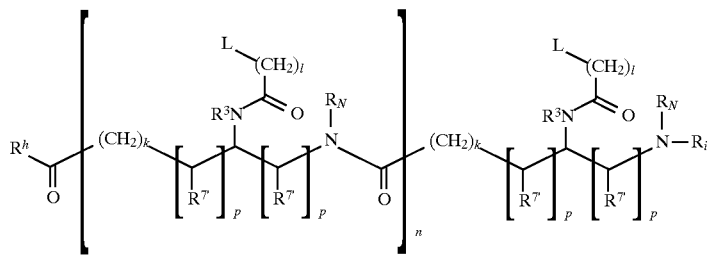

or formula

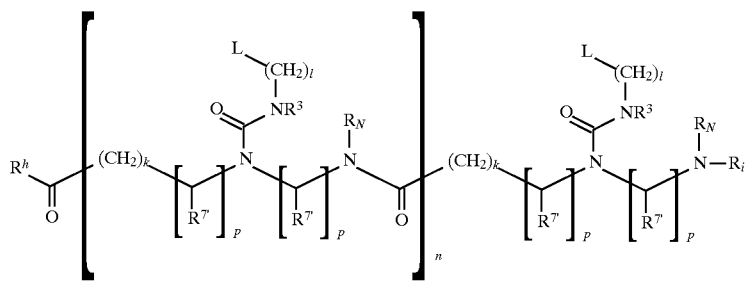

wherein:

each L is independently selected from the group consisting of hydrogen, phenyl, heterocyclic moieties, naturally occurring nucleobases, non-naturally occurring nucleobases and detectable labels;

each $R^{7'}$ is, independently, hydrogen, a side chain of a naturally occurring alpha amino acid, or Z, wherein Z is a detectable label;

n is an integer from 1 to 50;

each of k, l, and m is independently zero or an integer from 1 to 5;

p is zero, 1, or 2;

$R^h$ is OH, $NH_2$, OZ or -NHZ; and $R^i$ is H or Z; and $R_N$ is H or Z.

28. The method of claim 27 wherein:

each L is independently selected from the group consisting of the nucleobases thymine (T), adenine (A), cytosine (C), guanine (G) and uracil (U);

k and m are zero or 1; and n is an integer from 1 to 30.

29. The method of claim 28 wherein together said C, B, D and G groups are 2-aminoethylglycine.

30. The method of claim 1 further comprising the isolation and recovery of said hybridized moieties.

31. The method of claim 1 further comprising isolating and recovering said target oligonucleotide in substantially pure form.

32. A method of diagnosing a biological sample comprising detecting a target oligonucleotide according to the method of claim 1 or claim 2.

33. A method of analyzing a synthetic oligonucleotide sample comprising detecting a target oligonucleotide according to the method of claim 1 or claim 2.

34. A method of diagnosing a disease state comprising: selecting a target oligonucleotide indicative of the disease state; and detecting said target oligonucleotide according to the method of claim 1 or claim 2.

35. The method of claim 34 wherein said target oligonucleotide forms a part of the nucleic acid of an organism implicated to cause said disease state.

* * * * *

UNITED STATES PATENT AND TRADEMARK OFFICE
CERTIFICATE OF CORRECTION

PATENT NO. : 5,874,213
DATED : February 23, 1999
INVENTOR(S) : Cummins et al.

It is certified that error appears in the above-identified patent and that said Letters Patent is hereby corrected as shown below:

Column 3,
Line 57, please delete "containing" and insert therefor -- contains --;

Column 4,
Line 31, please delete "(CR$^6$R$^7$)" and insert therefor -- (CR$^6$R$^7$)$_z$ --;

Column 5,
Line 26, please delete "hybriized" and insert therefor -- hybridized --;

Column 7,
Line 29, please delete "referree" and insert therefor -- referred --;

Column 8,
Line 24, please delete "sequence" and insert therefor -- sequences --;
Line 42, please delete "type" and insert therefor -- types --;

Column 11,
Line 61, please delete "form" and insert therefor -- formed --;
Line 62, please delete "preformed" and insert therefor -- performed --;

Column 13,
Line 7, please delete "preformed" and insert therefor -- performed --.

Signed and Sealed this

Twenty-third Day of April, 2002

Attest:

*Attesting Officer*

JAMES E. ROGAN
*Director of the United States Patent and Trademark Office*